(12) United States Patent
Neuberger

(10) Patent No.: US 10,463,431 B2
(45) Date of Patent: Nov. 5, 2019

(54) DEVICE FOR TISSUE REMOVAL

(71) Applicant: Biolitec Pharma Marketing Ltd., F.T. labuan (MY)

(72) Inventor: Wolfgang Neuberger, Dubai (AE)

(73) Assignee: Biolitec Unternehmensbeteiligungs II AG, Vienna (AT)

( * ) Notice: Subject to any disclaimer, the term of this patent is extended or adjusted under 35 U.S.C. 154(b) by 0 days.

(21) Appl. No.: 14/781,787

(22) PCT Filed: Apr. 1, 2014

(86) PCT No.: PCT/IB2014/060360
§ 371 (c)(1),
(2) Date: Oct. 1, 2015

(87) PCT Pub. No.: WO2014/162268
PCT Pub. Date: Oct. 9, 2014

(65) Prior Publication Data
US 2016/0038236 A1 Feb. 11, 2016

Related U.S. Application Data

(60) Provisional application No. 61/807,137, filed on Apr. 1, 2013.

(51) Int. Cl.
*A61B 18/00* (2006.01)
*A61B 18/20* (2006.01)
*A61B 18/22* (2006.01)

(52) U.S. Cl.
CPC .... *A61B 18/22* (2013.01); *A61B 2018/00547* (2013.01); *A61B 2018/00577* (2013.01);
(Continued)

(58) Field of Classification Search
CPC ........ A61B 18/22; A61B 2017/320008; A61B 2018/00547; A61B 2018/00577;
(Continued)

(56) References Cited

U.S. PATENT DOCUMENTS 5,320,620 A * 6/1994 Long ............... A61B 18/22
606/16
5,688,261 A * 11/1997 Amirkhanian ........ A61B 18/22
606/13

(Continued)

*Primary Examiner* — Lynsey C Eiseman
*Assistant Examiner* — Jonathan Kuo
(74) *Attorney, Agent, or Firm* — B.J. Associates; Bolesh J. Skutnik

(57) ABSTRACT

Improved device and method for safe, accurate, efficient surgical procedures are disclosed. A preferred device is a waveguide assembly for delivering electromagnetic radiation to a tissue comprising a waveguide with a multi-facetted tip and a cap over the 5 multi-facetted tip. Preferably the waveguide is an optical fiber. The cap is a protective, reinforced cap fused to the optical fiber's tip as an integral part of it and comprises an axially-extending portion oriented at a predetermined angle relative to the elongated axis of the optical fiber. A method of manufacturing special waveguide caps is provided. The optical fiber assembly delivers high power electromagnetic radiation in lateral direction 10 with respect to the elongated axis of the optical fiber, determined by the multiple-facetted tip, the slant angles of the optical fiber's core, and the orientation of the cap's axially-extending portion. A method for removing unwanted tissue like in benign prostatic hyperplasia treatments is also provided.

11 Claims, 6 Drawing Sheets

(52) U.S. Cl.
CPC ............ *A61B 2018/00785* (2013.01); *A61B 2018/00904* (2013.01); *A61B 2018/2035* (2013.01); *A61B 2018/2255* (2013.01); *A61B 2018/2272* (2013.01); *A61B 2018/2288* (2013.01)

(58) Field of Classification Search
CPC .......... A61B 2018/00785; A61B 2018/00904; A61B 2018/2035; A61B 2018/2255; A61B 2018/2272; A61B 2018/2288
USPC .................................. 606/13–19; 607/88–93
See application file for complete search history.

(56) References Cited

U.S. PATENT DOCUMENTS

| | | | |
|---|---|---|---|
| 5,707,368 A * | 1/1998 | Cozean | A61B 18/22 606/15 |
| 5,708,735 A * | 1/1998 | Benson | G01N 21/553 356/445 |
| 6,699,239 B1 * | 3/2004 | Stiller | A61B 18/22 606/13 |
| 7,068,882 B2 * | 6/2006 | Saito | G02B 6/2552 385/123 |
| 2002/0159488 A1 * | 10/2002 | Wolak | G02B 6/262 372/36 |
| 2008/0317429 A1 * | 12/2008 | Boutoussov | A61B 18/22 385/146 |
| 2011/0082452 A1 * | 4/2011 | Melsky | A61B 18/24 606/15 |
| 2011/0295347 A1 * | 12/2011 | Wells | A61N 5/0601 607/89 |

* cited by examiner

Figure 2
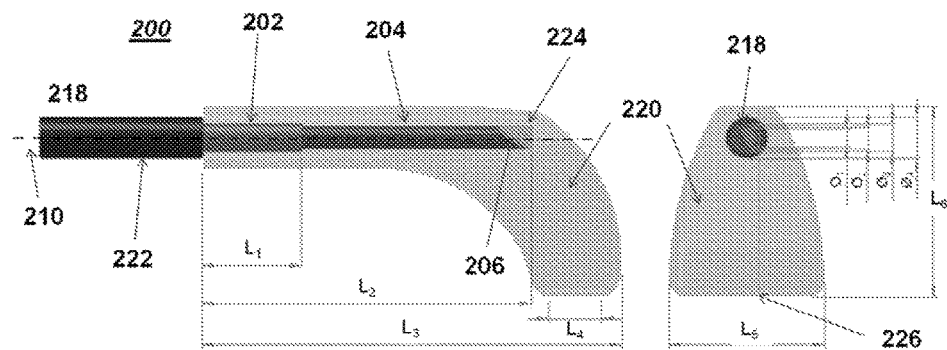
Fig. 2a
Fig. 2c
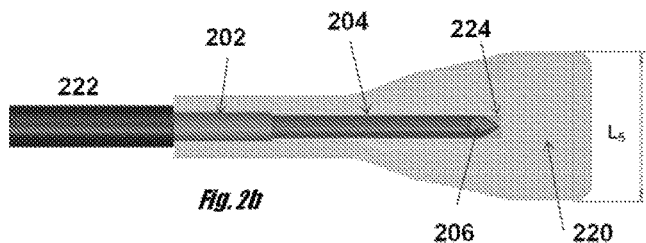
Fig. 2b

Figure 4
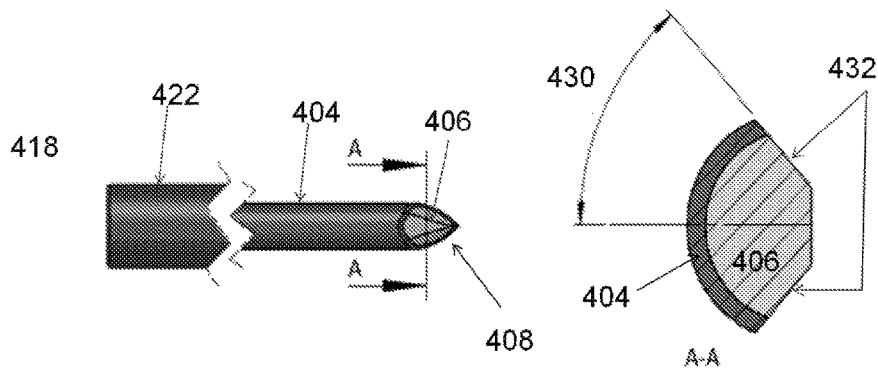
*Fig. 4a*
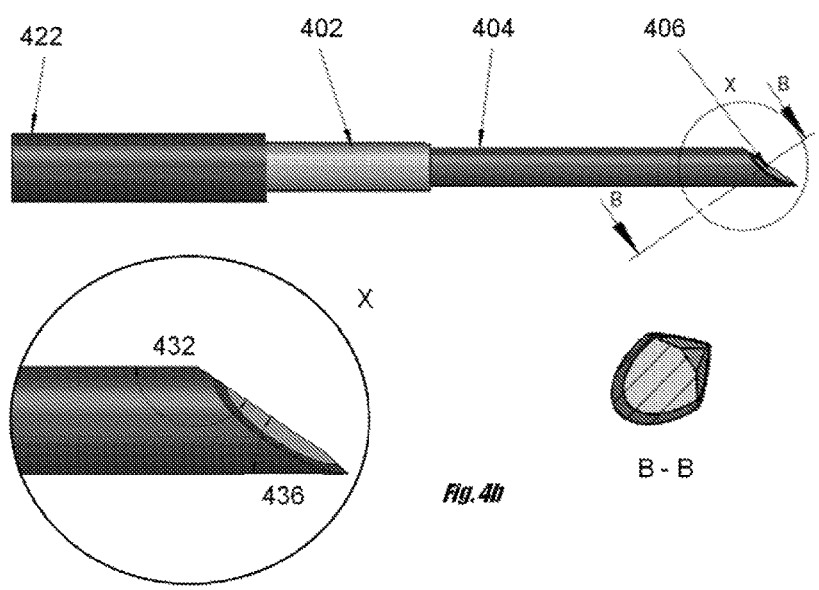
*Fig. 4b*

Figure 6
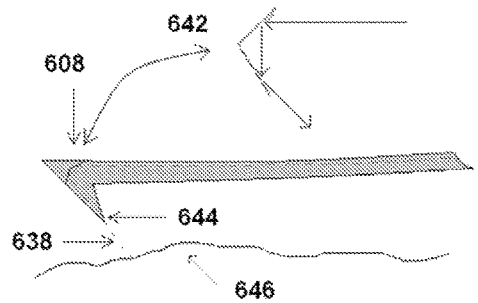
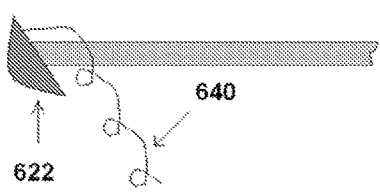
Fig. 6b
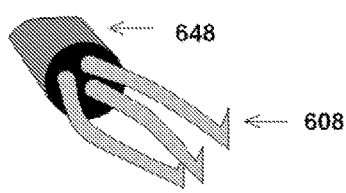
Fig. 6c
Figure 7
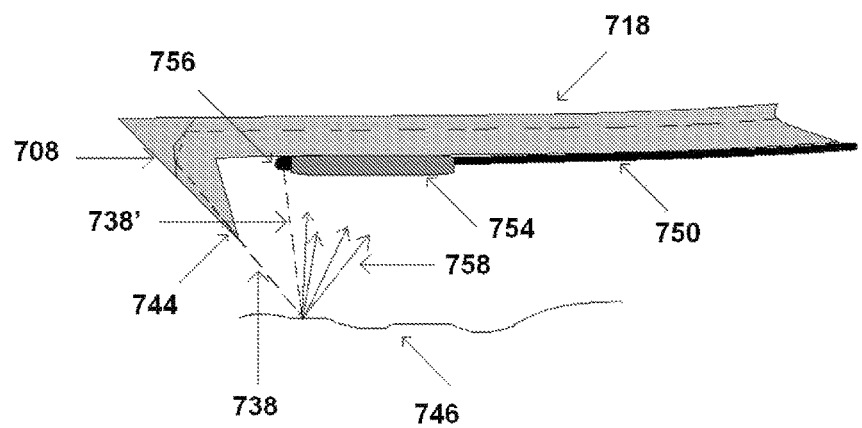

DEVICE FOR TISSUE REMOVAL

CROSS REFERENCE TO PRIORITY APPLICATION

This patent application claims priority to U.S. provisional patent application No. 61/807,137, filed on Apr. 1, 2013, by Wolfgang Neuberger entitled, "DEVICE FOR TISSUE REMOVAL" which is hereby expressly incorporated by reference in its entirety as part of the present disclosure.

BACKGROUND OF THE INVENTION

1. Field of the Invention

The present invention relates in general to surgical devices and methods for treatment of a body, and more particularly to devices and methods for transferring electromagnetic radiation to the body along or through a flexible conduit such as a waveguide.

2. Information Disclosure Statement

Laser ablation is used in a wide range of medical applications for the purpose of vaporizing tissue in order to remove mass of unwanted tissue or an obstruction. Different types of laser ablation devices operating at specific laser wavelengths and powers are commonly used for this variety of applications. In general, for a laser to ablate tissues the power density or fluence must be high, consequently, high power laser sources are required for vaporizing tissue and finishing the procedures in a reasonable period of time. However, undesirable effects like the destruction of laser-irradiated tissue or damage to optical components also result from laser ablation. Hence, there is a need of methods and devices that effectively deliver high-power laser radiation to tissue in a safe, precise and reliable manner while preserving the optical components and protecting healthy tissue surrounding the treatment site.

In an attempt to overcome these drawbacks, US Patent Application Publication No. 2011/0160713, and International Publication No. WO 2011/037651 both by Neuberger disclosed an optical fiber set with an asymmetric distal end configuration, comprising a bent tip fiber with a fused sleeve and a rotatable connector. The main difference with this invention is that the clad, core and cap of the optical fiber set are bent and define the tissue-contacting surface. A disadvantage of this configuration is that the stability of the optical fiber is reduced and undergoes degradation because the fiber tip is close or in contact with tissue. Present invention overcomes this drawback and provides a simpler device easy to fabricate and with bigger tissue-contacting surface, reducing the treatment time while enhancing the ablation procedure.

A side-firing optical surgical fiber assembly is disclosed in International Publication No. WO 2012/112386 by Tumminelli. The side-firing assembly intends to overcome the laser-induced pitting caused by one or more damage mechanisms by hardening the outer surface of the capillary, specifically, by creating a relatively high compressive stress in the surface. This invention requires specific materials and parameters leading to a complex fabrication process. In contrast, the devices and methods of present invention are easy to manufacture, more stable and provide a range of predetermined orientations of the laser beam in order to obtain a device that can be easily and efficiently operated by the physician.

Due to the disadvantages and deficiencies of current waveguide devices used in high power medical applications, a need exists for a device that provides a stable, safe and robust alternative which significantly reduces the damage to the waveguide devices caused by back-reflection of laser radiation, water-vapor bubbles, or ablated material depositing on the tip. Furthermore, there remains a need for quicker and more efficient procedures, causing less stress on patients and requiring less time of the physician.

OBJECTIVES AND BRIEF SUMMARY OF THE INVENTION

It is an objective of the present invention to provide a device and method for improved surgical procedures, which mainly involve tissue ablation/removal.

It is also an objective of the present invention to provide a device and method for removing unwanted tissue by means of laser irradiation while preserving surrounding healthy tissue.

It is another objective of the present invention to provide a waveguide assembly for high power applications with little or no degradation and enhanced durability.

It is yet another objective of the present invention to provide a method of manufacture a waveguide assembly for high power applications withstanding the delivery of high power and energy with enhanced capability and durability.

Briefly stated, an improved device and method for safe, accurate and efficient surgical procedures are disclosed. The disclosed device is a waveguide assembly for delivering electromagnetic radiation to a tissue comprising a waveguide with a multi-facetted tip and a cap that covers the multi-facetted tip. Preferably the waveguide is an optical fiber. The cap is a protective and reinforced cap fused to the optical fiber's tip as an integral part of it and comprises an axially-extending portion oriented at a predetermined angle relative to the elongated axis of the optical fiber. A method of manufacturing a waveguide cap is also provided. The optical fiber assembly delivers high power electromagnetic radiation in lateral direction with respect to the elongated axis of the optical fiber, determined by the multiple-facetted tip, the slant angles of the optical fiber's core, and the orientation of the cap's axially-extended portion. A method for removing unwanted tissue like in benign prostatic hyperplasia treatments is also provided as an example.

The above and other objects, features and advantages of the present invention will become apparent from the following description read in conjunction with the accompanying drawings.

BRIEF DESCRIPTION OF FIGURES

FIG. 2a depicts side view of one embodiment of an optical fiber assembly comprising an optical fiber and a cap.

FIG. 2b shows a front view of one embodiment of the cap that covers the optical fiber tip.

FIG. 2c depicts a top view of the optical fiber assembly comprising an optical fiber and a cap.

FIG. 4a is a bottom view of one embodiment of optical fiber and a cross sectional view A-A of the multiple-facetted tip showing preferred angle dimensions.

FIG. 4b is a side view of one embodiment of the optical fiber comprising the optical fiber assembly, showing an amplified view X of the multiple-facetted tip with preferred angle dimensions, and a cross sectional view B-B of the multiple-facetted tip.

FIG. 6a depicts side view of fiber tip of a preferred embodiment.

FIG. 6b shows fiber tip of a preferred embodiment as seen from below.

FIG. 6c depict fiber tip of a preferred embodiment.

FIG. 7 shows a preferred embodiment of present invention including tissue-type detecting safety system.

DETAILED DESCRIPTION OF PREFERRED EMBODIMENTS

Figure 1:
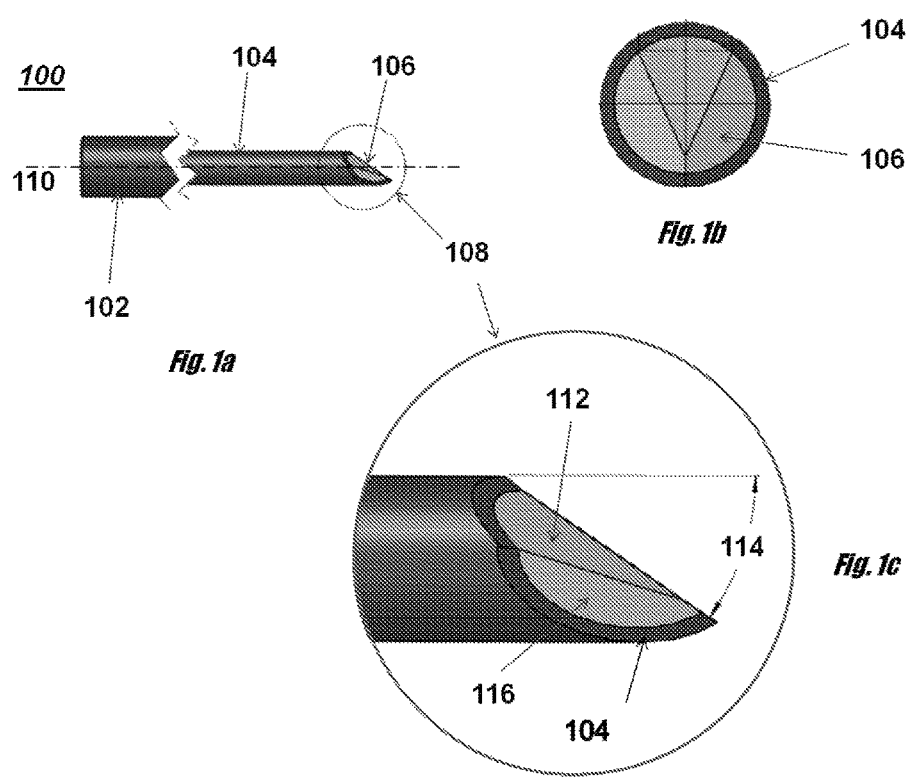
FIG. 1a shows a top side view of an embodiment of optical fiber of the waveguide assembly of present invention.
FIG. 1b shows a top front view of one embodiment of the multiple-facetted tip of the optical fiber comprising the waveguide assembly.
FIG. 1c is an amplified view of the multiple-facetted tip of the optical fiber showing two of the three facets.

A common use of medical lasers is to vaporize a tissue for the purpose of removing an obstruction or mass of unwanted tissue. The high power required for vaporizing tissue needs to be safely delivered in a precise and reliable manner. Due to the key features of the methods and devices hereby provided, the unwanted mass is effectively ablated/removed while preserving surrounding healthy tissue. Furthermore, the medical treatments performed with the devices and methods hereby presented are faster, and successfully overcome the disadvantages of prior art techniques and apparatuses.

Present invention provides a medical laser treatment device incorporating at least one optical fiber and a distal tip configured specifically for effective tissue ablation/removal involving high-power laser radiation. It also provides medical laser treatment device incorporating at least one optical fiber and a distal tip configured specifically for enabling the resection of small tissue pieces in the course of its movement against tissue when laser radiation is applied, thus enhancing the speed of the treatment and/or providing tissue samples for medical analysis.

The poor outcome of prior art devices is evident especially when those tools are used in contact mode. When the tips of the optical fibers of prior art devices are in contact with tissue, they are burnt and/or broken and their efficiency is greatly diminished. The main reason is because during contact lasing, tissue and blood adhere to the fiber tip surface limiting further laser transmission. Such tissue residues create high power densities and temperatures at the tip, which then cause a variety of degradation processes to be initiated. The waveguide assembly hereby provided overcomes these drawbacks as the tip of the fiber is not in direct contact with, nor close to ablating tissue; it is the cap that is in direct contact with tissue and effectively guides high power for long periods of time without burning or breaking the tip. Consequently, the medical treatments performed with the devices provided are used in contact or non-contact mode indiscriminately. The advantage of delivering electromagnetic radiation with the devices provided in contact mode is that energy loss is highly reduced and the high power is effectively concentrated. In turn, fiber durability is considerably longer because of the novel structure of the present invention, overcoming early failure issues with prior art fibers.

Another potential disadvantage of tissue removal applications by laser ablation, such as the treatment of being prostatic hyperplasia, is the need of longer lasing times and high power. Even though the laser devices are able to deliver high power for long periods, the optical fiber that delivers radiation to the tissue suffers larger transmission losses and degradation of its tip during this interaction with tissue. This degradation converts the laser power to heat and leads to increasing energy loss. The continued lasing and mechanical breakdown of the fiber leads to failure of the fiber tip and the spalling of glass fragments into the tissue bed. One of the main advantages of the current design is that the waveguide assembly is much more stable when used in high power applications for tissue removal, such as tissue ablation in urological treatments. There is virtually no fiber degradation during the treatment and the optical fiber durability is much longer than for the standard optical fibers. In particular, present invention provides optical fiber design for high power lasers, having outputs of greater than or equal to 50 Watts to about 400 Watts and resisting laser energy up to more than 800 kJ. For these reasons, present invention is particularly appropriate for the medical treatment of benign prostate hyperplasia (BPH), ablation of unwanted tissue, removing obstructions, and similar medical treatments.

In one embodiment, present invention is a waveguide assembly for delivering electromagnetic radiation to a tissue, that comprises at least one flexible waveguide optically connectable by its proximal end to a source of radiation; and a cap/sleeve that covers said waveguide's distal end. One of the distinguishing features is that the cap comprises an axially-extending portion oriented at a predetermined angle relative to the elongated axis of said waveguide. In one embodiment, the cap axially-extending portion is expanded compared with the dimensions of the optical fiber's distal end. In a preferred embodiment, the waveguide assembly has an off-axis configuration comprising a waveguide with a multi-facetted tip and a bent cap that covers the waveguide's multi-facetted tip and defines a tissue-contacting surface, wherein the electromagnetic radiation beam is delivered laterally with respect to the elongated axis of the waveguide.

The waveguide assembly is connected to an electromagnetic radiation delivery device at its proximal end. The preferred electromagnetic radiation delivery is a high power laser device, diode laser, or LED device, but other electromagnetic radiation sources may be included. At its distal end, the waveguide assembly defines a tissue-contacting surface that is configured to be placed into contact with tissue to be treated, in order to transmit electromagnetic radiation energy from the waveguide through the tissue-contacting surface to ablate the tissue in contact with the tissue-contacting surface.

The waveguide comprising the waveguide assembly is preferably an optical fiber which defines an elongated axis with a multiple-facetted distal end. The cap or sleeve that covers the optical fiber's multiple-facetted end comprises an axially-extending portion oriented at a predetermined angle relative to the elongated axis of the waveguide. This design results in an electromagnetic radiation beam directed laterally with respect to the elongated axis of the waveguide; following the orientation of the cap. In one embodiment, the cap/sleeve is bent at a predetermined angle with respect to the elongated axis of the waveguide and forms an extended portion. In one embodiment, this angle is substantially perpendicular to the elongated axis of the waveguide. A tissue-contacting surface is defined by the plane located at the cap's distal end; parallel to the elongated axis of the waveguide if the bent angle is perpendicular to the elongated axis of the waveguide.

Preferably, the cap/sleeve is a protective cap fused to the waveguide's distal end as an integral part of it. In preferred embodiments, the waveguide assembly is an off-axis emitting fiber optic medical treatment device.

It has to be understood that present embodiments show the use of a single optical fiber, however the same embodiments are applicable for waveguide assemblies comprising more than one optical fiber, as might be the case if multiple electromagnetic energy sources are employed.

FIG. 1a-c shows optical fiber 100 of a preferred embodiment of the waveguide assembly without a cap. FIG. 1a shows a side view of optical fiber 100 comprising jacket 102, cladding 104 and core 106, with multiple-facetted tip 108 for directing electromagnetic radiation laterally with respect to elongated axis 110 of optical fiber 100. To further enhance the reflective power of multiple-facetted tip surface a reflective layer may be formed thereon, as is known in the optical arts. FIG. 1b shows a top front view of one embodiment of multiple-facetted tip 108 comprising three facets in core 106, surrounded by cladding 104. FIG. 1c is an amplified view of multiple-facetted tip 108 with three facets, wherein central facet 112 is formed by a core that is slanted at a given angle 114 to elongated axis 110 of optical fiber 100, and lateral facets 116 which are also formed by a core that is slanted at a given angle to elongated axis 110 of optical fiber 100. In one embodiment, slant angle 114 is between about 30 to about 50 degrees, and more preferably between about 32 to about 36 degrees.

Preferably, the cap at the tip of present invention has an expanded beam tip with a bigger tip surface than commonly used optical fibers for delivering electromagnetic radiation for tissue removal, increasing the ablation velocity and reducing the time of the medical procedure. This is achieved by designing a cap as shown in FIG. 2a-c.

FIG. 2a shows side view of optical fiber assembly 200 comprising optical fiber 218 and cap 220. Optical fiber 218 comprises protective jacket 222, outer cladding 202, inner cladding 204 and core 206, with multiple-facetted tip for directing electromagnetic radiation laterally with respect to elongated axis 210 of optical fiber 218. Cap 220 comprises an axially-extending portion oriented at a predetermined angle relative to elongated axis 210 of optical fiber 218. To enhance the reflective power of multiple-facetted tip, gap 224 is formed between the multiple-facetted tip of optical fiber 218 and cap 220. FIG. 2c shows a front view of cap 220, the relative location of optical fiber 218, and tissue-contacting surface 226 that is configured to be placed into contact with tissue to be treated, in order to transmit electromagnetic radiation energy to ablate the tissue. And FIG. 2b is a top view of protective jackets 222 and buffer 202, cladding 204 and core 206, with multiple-facetted tip. Cap 220 comprises an expanded tip that increases the ablation velocity of optical fiber assembly 200. In one embodiment, the dimension shown in FIG. 2 are $L_1 \neq L_2 \neq L_3 \neq L_4 \neq L_5 \neq L_6$; wherein $L_4 < L_1 < L_5 < L_6 < L_2 < L_3$; and $\emptyset_1 < \emptyset_2 < \emptyset_3 < \emptyset_4$. In one embodiment, the protective jacket is made of a modified (ethylene-tetrafluoroethylene) fluoroplastic, the buffer is made of nylon, the inner cladding is made of silica/doped silica, the core is made of doped silica and the cap is made of a special clear silica glass, wherein the cap and the outer surface of the inner cladding are made of substantially the same material. Preferably, the cladding is made of glass, the cap/sleeve is made of a special clear silica glass, and the cap/sleeve is thermally fused to the cladding substantially throughout the interface between the sleeve and the cladding. Such a fused cap also acts as reinforcement, allowing fiber to withstand high energies.

In one embodiment, the cap is made of a clear quartz glass and a method for manufacturing said cap comprises the steps of 1) casting sol-fluid containing $SiO_2$ particles; 2) pouring said sol-fluid into a mould with the cap's predetermined shape and allowing said sol-fluid to thicken into a gel, 3) drying the gel; 4) sintering the gel; and 5) cooling the product immediately. Preferably, the $SiO_2$ particles are nano-scaled $SiO_2$ particles and the casting is preformed practically free of all contaminations and bubbles. The mould has the desired geometrical shape and high grade surface quality. After drying the gel, intermediate product with a chalk-like appearance with pores filled by a special gas is obtained. The sintering step comprises a thermal treatment step with temperatures between 1000° C. and 1400° C. (1832° F.-2552° F.) wherein the pores collapse and cause a three dimensional shrinkage to the final desired measures of the cap. The immediate cooling step avoids a possible viscose deformation of the cap.

By using a multiple-facetted tip and controlling the slant angles of the core, it is possible to build the cap with a predetermined orientation and predefine a desired direction of the emitted electromagnetic radiation beam. It is possible to control the orientation of the cap's axially-extending portion with the slant angles of the facets. This new design provides an easy to use device for improved handling and efficiency, wherein the angle of the reflected light at the tip of the optical fiber is determined by the number of facets and their angles in relation to the elongated axis of optical fiber, which in turn determines the orientation of the cap's bent portion.

In one embodiment, the waveguide assembly has a rotatable connector at its proximate end which allows rotating movements of the tip for smooth and precise movements in circular fashion. However, due to this new design, the waveguide assembly is also able to be used without a manipulator/rotator connector because the movements of the tip are performed in back and forward direction, with virtually no rotation to the left and right directions required.

Figures 3, 3A, 3B:
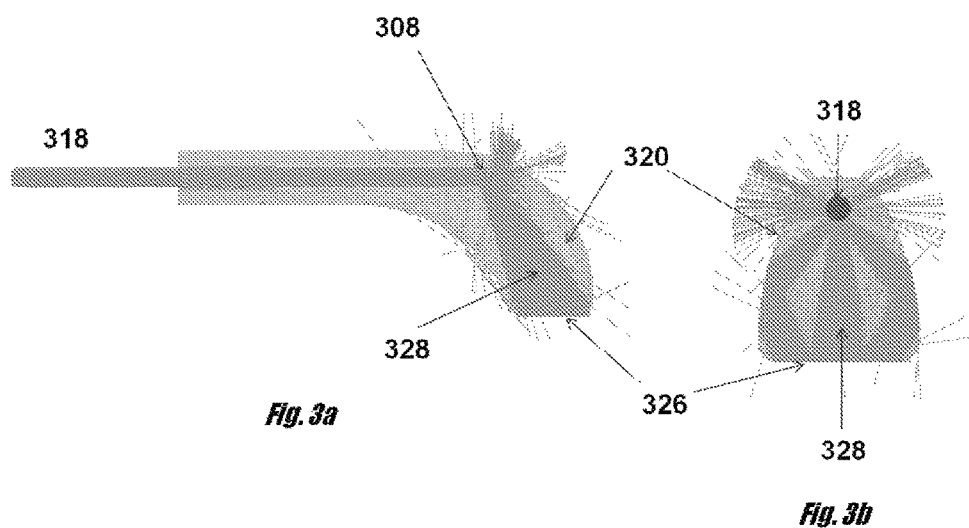
FIG. 3a is a side view of one embodiment of off-axis emitting fiber optic device showing the direction of the beam.
FIG. 3b is a front view of one embodiment of the off-axis emitting fiber optic device, showing the direction of the beam.

In addition, the multiple-facetted tip and the bent cap provide a more homogenous beam profile with essentially no or minimal stray light. All the electromagnetic radiation generated by the electromagnetic radiation device is effectively guided through the bent cap to the tissue and substantially no light is guided in the axial direction of the waveguide. All the energy is effectively concentrated in a single direction and there is virtually no energy loss because the electromagnetic radiation does not follow paths other than that intended in this special design. FIG. 3a-b depicts one embodiment of off-axis emitting fiber optic device showing the direction of the beam. FIG. 3a is a side view of off-axis emitting fiber optic device and FIG. 3b is a front view of off-axis emitting fiber optic device. Optical fiber 318 has multiple-facetted tip 308 which is covered by cap 320 having a predetermined orientation. The slant angle of multiple-facetted tip 308 and the orientation of cap 320 define a desired direction of laser radiation beam 328, which is effectively concentrated in a single direction laterally with respect to the elongated axis of optical fiber 318. Laser radiation beam 328 is transmitted through tissue-contacting surface 326 to ablate the tissue in contact with tissue-contacting surface 326.

Another embodiment, optical fiber 418 of the off-axis optical fiber device is shown in FIG. 4a-b. FIG. 4a is a bottom view of optical fiber 418 showing jacket 422, inner cladding 404, core 406 and multiple-facetted tip 408 with three facets, wherein the sectional view A-A illustrates angle 430 of lateral facets 432 in core 406 surrounded by cladding 404. In this embodiment, angle 430 is between about 40 to about 60 degrees, and more preferably between about 45 to about 53 degrees.

FIG. 4b is a side view showing jacket 422, outer cladding 402, inner cladding 404, core 406 and an amplified view of multiple-facetted tip 408, wherein core 406 has a slant angle. Angles 434 and 436 are also shown in the amplified view, and in this embodiment, angle 434 is between about 132 to about 160 degrees, and more preferably between about 142 to about 150 degrees; and angle 436 is between about 30 to about 40 degrees, and more preferably between about 32 to about 36 degrees In another preferred embodiment, the tissue-contacting surface of the optical fiber cap assembly has a sharp edge or a rough surface. Preferably, the section that forms the tissue-contacting surface is shaped like a scraper blade or snow plough, while another section of the cap maintains a rounded shape, to advance the fiber inside the body without damaging the tissue in areas where tissue removal is not desired. Laser radiation exits the optical fiber assembly at blade end in a lateral direction with respect to the elongated axis of optical fiber and the scraper blade in contact with tissue improves the removal procedure. This embodiment allows a combined mechanical and optical effect by removing tissue pieces faster than prior art methods or devices that rely only on a laser vaporization effect. Thus, depending on emission settings, type of energy applied and procedure technique, effect of radiation emitted will be to cut, vaporize, or coagulate target tissue or a combination of these. For example, laser energy set at continuous wave configuration at a power of 250 W and a wavelength of 980 nm will detach and vaporize great amounts of target soft tissue when surgeon applies scraping movements to said tissue while lasing.

Figure 5:
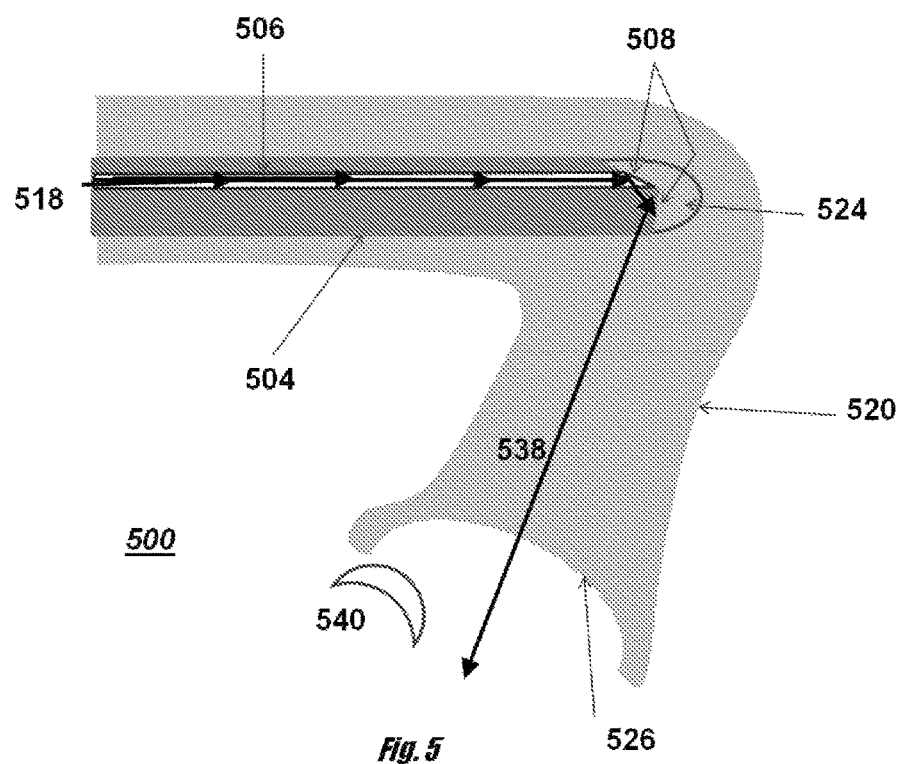
FIG. 5 is a side view of one embodiment of an off-axis fiber optic device comprising an eccentric core, an optical fiber with a multiple-facetted tip and a cap defining an air gap between the optical fiber tip and the cap.

A side view of another embodiment is shown in FIG. 5. Off-axis emitting fiber optic device 500 comprises inner cladding 504, eccentric core 506, multiple-facetted tip 508 and sealed cap 520 fixedly secured to the end of optical fiber 518. Laser radiation 538 is guided through eccentric core 506 and is reflected after impinging onto multiple-facetted tip 508. Gap 524 formed between optical fiber 518 and cap 520 defines an air or other gas interface at multiple-facetted tip 508. Owing to the different indices of refraction between optical fiber 518 and gap 524, and the angles of multiple-facetted tip 508, off-axis emitting fiber optic device 500 delivers laser radiation 538 in a generally lateral direction with respect to the elongated axis of optical fiber 518. Tissue-contacting surface 526 of sealed cap 520 has an essentially concave shape, like a snow plough. Off-axis emitting fiber optic device 500 vaporizes and/or scrapes off tissue chips 540. Scraped off tissue chips 540 can be collected, if desired, and used as sample tissue for analyzing presence of cancerous cells. With proper scraping movements, off-axis emitting fiber optic device 500 is used for enabling the resection of small tissue pieces when laser radiation is applied, thus enhancing the speed of the treatment, and/or providing tissue samples for medical analysis.

In another embodiment, a scraper-shaped fiber tip is shown in FIGS. 6a-c. In FIG. 6a, light energy 638 exits distal fiber end 608 at scraper tip 644 due to a properly designed optic configuration 642, at a power and wavelength such that a large portion of target tissue 646 is vaporized or broken loose and scraped back under the main fiber towards the proximal end. With proper scraping movements, blade tip 644 is used to easily scrape or brush away loosened tissue chips 640 that have not been fully vaporized by lasing energy. FIG. 6b shows another view of scraper tip as seen from below. It can be appreciated that with proper scraping movements, scraped off tissue 640 is released such that it does not interfere with physician's field of view. Scraped off tissue chips 640 can be used as sample tissue for analyzing presence of cancerous cells or for other medical information. In another preferred embodiment, probe, as seen in FIG. 6c, is comprised of a shaft 648 containing more than one fiber where at least one of these fibers' distal end 608 is scraper/plough shaped.

In a preferred embodiment, a method for removing unwanted tissue comprises the steps of using the off-axis emitting fiber optic medical treatment device described in present invention and placing the tissue-contacting surface into contact with tissue to be treated; transmitting laser energy from the fiber through the tissue-contacting surface; moving the tissue-contacting surface and tissue relative to each other during the step of transmitting laser energy and ablating the tissue in contact with the tissue-contacting surface. The moving step includes moving the tissue-contacting surface in forward and backward directions with a sweeping motion across the tissue while ablating the contacted tissue. In a preferred embodiment, the method disclosed above is for treating benign prostatic hyperplasia, and the treated tissue is hyperplasic prostatic tissue.

It is important to note that different combinations of radius and angles are used in the design of the optical fiber assemblies disclosed in this invention. The exact values of radius and angles are chosen according to the treatment to be performed, considering accessibility, tissue characteristics, scope size, and other relevant parameters.

A further advantage of this invention is that it provides specially designed distal end and emission configuration for effective tissue elimination along with a safety sensing system capable of discriminating healthy tissue from unwanted tissue. In one embodiment, the waveguide assemblies described above include a safety system comprising an emitting beam and sensor attached to treatment optical fiber. Sensing system cuts off lasing energy when it detects that healthy tissue is being irradiated. Such healthy tissue has a different histological structure than unhealthy and consequently incident light radiation will reflect differently. Preferably, tissue detection system is achieved by integrating an additional small diameter fiber in parallel to scraper fiber as well as a light detecting sensor. Additional fiber emits a low energy light beam on target tissue. Sensor system can therefore, detect and identify backscattered radiation coming from irradiated tissue.

FIG. 7 shows another preferred embodiment of safety system described. Light energy 738 exits fiber end 708 at scraper blade tip 744 at a power and wavelength such that a large portion of target tissue 746 is either vaporized or broken loose. With proper scraping movements, blade tip 744 is used to easily scrape or push away broken loose tissue that has not been vaporized by lasing energy. Integrated to fiber 718 is safety system 750, comprising pulse emitter 752 and sensor 754. In a preferred embodiment, a pulse of light energy 738' is emitted from pulse emitter 756 toward target tissue 746. The scattered radiation 758 that backscatters to sensor 754 is collected with proper receiving optics and sent to detector (not shown). The signal in the detector is properly processed and converted into a valid numerical format that can be identified according to type of tissue. When system identifies that backscattered lights corresponds to tissue preprogrammed as "healthy", lasing is immediately stopped.

EXAMPLE 1

The optical fiber assembly of present invention is used for high power ablation of prostatic tissue for Benign Prostate Hyperplasia (BPH) treatments. The optical fiber assembly is inserted through the patient's urethra to convey laser radiation from laser source device to hyperplasic prostate in order to ablate prostate tissue. A cystoscope or resectoscope is used to access the treatment site and correctly place the optical fiber assembly at the treatment site. The tissue-contacting surface of the optical fiber assembly is in contact with tissue to be treated, and once the laser parameters are set at about 350 W in continuous mode, laser energy is transmitted through the tissue-contacting surface to the prostatic tissue to be removed. The whole procedure is monitored by endoscopic imaging. Laser energy is delivered while simultaneously moving the tissue-contacting surface and tissue relative to each other. The movements include moving the tissue-contacting surface in the forward and backward direction with a sweeping motion across the tissue for ablating the contacted tissue. Saline solution is used during the procedure particularly for cooling but also for having a clean view during the procedure. The main advantage is that this new optical fiber assembly is stable and resists a power of up to 400 W and more than 800 kJ with substantially no degradation.

The optical fiber assembly conveys laser radiation from laser source device operating at a wide range of laser wavelengths. For instance, for urological treatments laser source device can operate at any of 810 nm, 940 nm, 980 nm, 1320 nm, 1500 nm, 1940 nm, etc. preselected wavelengths. In a preferred embodiment, wavelengths of 980 nm, 1470 nm or both in an appropriate combination can be used, with total power levels of up to and beyond 300 W.

EXAMPLE 2

In another example, the optical fiber assembly of present invention is used for the removal of adipose tissue in aesthetic procedures. Once the areas to be treated are properly identified and marked, the parameters of the laser source are set. In this example, laser energy is delivered in continuous mode at a power of about 250 W and a wavelength of 980 nm. An incision is made and the optical fiber assembly's tip is placed at the treatment site. When the tissue-contacting surface of the optical fiber assembly is placed into contact with the adipose tissue to be treated, the surgeon delivers laser energy from the fiber through the tissue-contacting surface to the adipose tissue. The surgeon applies the laser energy while moving the optical fiber assembly's tissue-contacting surface in the forward and backward direction with a sweeping motion across the tissue in order detach and vaporize great amounts of soft tissue. This novel design allows for more effective tissue ablation and removal, therefore procedures are more reliable and procedure times are decreased.

EXAMPLE 3

In another example, BPH is treated with the off-axis emitting fiber optic device as described in FIG. 5. First, laser parameters are set at high energy, preferably near 300 W in continuous wave mode. Then, the fiber optic device is inserted into body, proximate to and aimed at target tissue. Procedure is preferably monitored online by endoscopic imaging. Next, the physician begins irradiation using scraping movements and gets tissue samples for biopsy. Then, he applies further laser energy while simultaneously making scraping movements in contact with target tissue, such that the laser energy breaks up and ablates target tissue and the scraping blade easily scrapes remaining tissue. Consequently, part of tissue is vaporized and another part of tissue is broken up and pushed away from field of view. Intermittently, target tissue may be irradiated in non-contact mode to coagulate existing blood and prevent bleeding where tissue was damaged to improve sight at treatment site. Finally, tissue that is broken up but not vaporized may be flushed out of body using saline solution, and collected if necessary for further medical analysis/testing These features allow for improved and enhanced treatment of diverse pathologies, making it possible to efficiently and easily reach and treat specific tissues. Although safety system is presently exemplified for BPH treatments and removal of adipose tissue, it is to be understood that this invention is appropriate for high power applications, such as, tissue removal virtually anywhere it is desirable or required, and those that require a stable and robust delivery device for guiding electromagnetic radiation to a treatment site.

Having described preferred embodiments of the invention with reference to the accompanying drawings, it is to be understood that the invention is not limited to these precise embodiments, and that those skilled in the art can effect changes and modifications without departing from the scope of the invention as defined in the appended claims.

What is claimed is:

1. A waveguide assembly, for delivering electromagnetic radiation to a tissue, comprising,
    at least one flexible optical fiber having an elongated axis comprising a proximal end optically connectable to a source of radiation and a multiple-facetted distal end consisting of three facets that are a central facet and one facet on either side of the central facet, wherein the central facet is slanted to the elongated axis of the optical fiber at an angle between 30 to 50 degrees and
    a cap /sleeve that covers said distal end of said optical fiber;
    wherein said cap/sleeve comprises an axially-extending portion oriented at a predetermined angle relative to the elongated axis of said optical fiber in a direction opposite said central facet, and wherein said assembly is configured to emit radiation in a single lateral direction with respect to the elongated axis of said optical fiber through the axially-extending portion of the cap.

2. The waveguide assembly according to claim 1, wherein cap/sleeve defines a tissue-contacting surface configured to be placed into contact with tissue to be treated in order to transmit electromagnetic radiation energy from the optical fiber through said tissue-contacting surface to ablate/remove, the tissue in contact with said tissue-contacting surface.

3. The waveguide assembly according to claim 2, wherein said tissue-contacting surface is defined by the plane at the cap/sleeve's distal end parallel to the elongated axis of the optical fiber.

4. The waveguide assembly according to claim 1, wherein said tissue-contacting surface has a shape that enables the resection of small tissue pieces for enhancing the speed of the treatment and/or for providing tissue samples for medical analysis.

5. The waveguide assembly according to claim 4, wherein said shape is concave.

6. The waveguide assembly according to claim 1, wherein said cap/sleeve is a protective and reinforced cap fused to the optical fiber distal end as an integral part of it.

7. The waveguide assembly according to claim 1, wherein said angle of said central facet is slanted to the elongated axis of optical fiber at an angle between about 32 to 36.

8. The waveguide assembly according to claim 1, wherein said cap/sleeve comprises an expanded portion compared with the dimensions of the optical fiber distal end to increase the ablation velocity and reduce the time of the medical procedure.

9. The waveguide assembly according to claim 1, wherein the reflective power of said multi-facetted distal end is further enhanced by an air gap between the multiple-facetted end of said optical fiber and said cap.

10. The waveguide assembly according to claim 1, wherein the reflective power of said multi-facetted distal end is further enhanced by a reflective layer on the facets of said multi-facetted end.

11. The waveguide assembly according to claim 1, wherein said radiation is delivered by an electromagnetic radiation delivery device selected from the group consisting of a high power laser device, a diode laser, or a LED device.

* * * * *